United States Patent
Wu et al.

(10) Patent No.: US 8,916,572 B2
(45) Date of Patent: Dec. 23, 2014

(54) BIS-QUINAZOLINE DERIVATIVES AS INHIBITORS FOR EPIDERMAL GROWTH FACTOR RECEPTOR (EGFR) TYROSINE KINASE

(71) Applicant: Tetranov International, Inc., New Brunswick, NJ (US)

(72) Inventors: Yusheng Wu, New York, NY (US); Chengshan Niu, Zhengzhou (CN); Dapeng Zou, Zhengzhou (CN); Jingya Li, Zhengzhou (CN); Ruiyun Guo, Zhengzhou (CN)

(73) Assignee: Tetranov International Inc., New Brunswick, NJ (US)

( * ) Notice: Subject to any disclaimer, the term of this patent is extended or adjusted under 35 U.S.C. 154(b) by 0 days.

(21) Appl. No.: 13/887,593

(22) Filed: May 6, 2013

(65) Prior Publication Data

US 2013/0296348 A1    Nov. 7, 2013

Related U.S. Application Data

(60) Provisional application No. 61/660,200, filed on Jun. 15, 2012.

(51) Int. Cl.
| *A01N 43/54* | (2006.01) |
| *A61K 31/517* | (2006.01) |
| *C07D 239/72* | (2006.01) |
| *C07D 401/00* | (2006.01) |

(52) U.S. Cl.
USPC ..................................... 514/266.1; 544/283

(58) Field of Classification Search
USPC ................................ 514/283, 284; 544/266.1
See application file for complete search history.

(56) References Cited

U.S. PATENT DOCUMENTS

| 5,747,498 | A | 5/1998 | Schnur et al. |
| 8,349,856 | B2 | 1/2013 | Qian et al. |
| 8,399,667 | B2 | 3/2013 | Bradbury et al. |
| 8,404,698 | B2 | 3/2013 | Lee et al. |
| 8,426,430 | B2 | 4/2013 | Zhang et al. |
| 8,431,586 | B2 | 4/2013 | Okano et al. |

OTHER PUBLICATIONS

Vippagunta et al (2001).*
Banker et al (1997) Wolff et al (1997).*
McMahon et al (2000) Pinedo et al (2000).*
Steven D. Young et al., *Antimicrobial Agents and Chemotherapy*, 2602-2065 (1995).

* cited by examiner

*Primary Examiner* — Paul V. Ward
(74) *Attorney, Agent, or Firm* — Fox Rothschild LLP; W. Jerry Liu

(57) ABSTRACT

Novel bis-quinazoline derivatives as tyrosine kinase inhibitors, synthesis of these compounds, and novel methods for treating tyrosine kinase mediated diseases or disorders using these compounds are disclosed. In particular, the present invention provides tethered quinazoline derivative dimers as inhibitors to the epidermal growth factor receptor (EGFR) tyrosine kinase, pharmaceutical compositions thereof, and their therapeutic uses for treating EGFR kinase-mediated diseases or disorders, such as various cancers, as well as synthetic methods for preparing these novel compounds.

18 Claims, No Drawings

BIS-QUINAZOLINE DERIVATIVES AS INHIBITORS FOR EPIDERMAL GROWTH FACTOR RECEPTOR (EGFR) TYROSINE KINASE

CROSS REFERENCE TO RELATED APPLICATIONS

This application claims priority benefit under 35 U.S.C. §119(e) to U.S. Provisional Patent Application No. 61/660,200, filed on Jun. 15, 2012, which is hereby incorporated by reference in its entirety.

FIELD OF THE INVENTION

This invention relates to novel bis-quinazoline derivatives (or tethered quinazoline derivative dimers) as tyrosine kinase inhibitors, their synthesis and their use for treating a tyrosine kinase mediated diseases or disorders.

BACKGROUND OF THE INVENTION

Tyrosine kinase receptors are trans-membrane proteins involved in signal transduction. They propagate growth factor signals from the cell surface to intracellular processes that control critical functions such as growth, differentiation, angiogenesis and inhibition of apoptosis. In malignancies, these signaling pathways are often exploited to optimize tumor growth and metastasis. One such family of receptor tyrosine kinases is the epidermal growth factor receptor (EGFR) tyrosine kinase. These receptors are overexpressed in a wide variety of major human cancers such as brain, lung, squamous cell, bladder, gastric, breast, head and neck, esophageal, gynecological and thyroid cancers. Thus, an inhibitor of EGFR receptor tyrosine kinase is useful for treating a variety of human cancers.

Various pre-clinical and clinical studies have demonstrated that EGFR tyrosine kinase inhibitors can block cancer cell proliferation, metastasis and other EGFR-related signal transduction responses to achieve clinical anti-tumor therapeutic effects.

Erlotinib, an EGFR kinase inhibitor as disclosed in U.S. Pat. No. 5,747,498, was approved by US FDA for advanced non-small cell lung cancer and pancreatic cancer treatment in 2004, and has been clinically useful since. Subsequently, quinazoline-based EGFR kinase inhibitors have been extensively studied in search for new anti-cancer agents. Recent U.S. patents issued on quinazoline derivatives as potential therapeutic agents include U.S. Pat. Nos. 8,431,586; 8,426,430; 8,404,698; 8,399,667; and 8,349,856, just naming a few. These demonstrate that, due to the high demand of novel and better anticancer agents, new strategies and methods for discovering novel tyrosine kinase inhibitors as useful therapeutic agents are still being actively pursued.

SUMMARY OF THE INVENTION

The present invention provides a novel approach to discovery of new quinazoline-based EGFR kinase inhibitors as useful anticancer agents. Specifically, the invention provides novel EGFR kinase inhibitors comprising two quinazoline derivative moieties linked by a tether group, as characterized by the general structure of formula (I), pharmaceutical compositions comprising these compounds, use of these compounds for making medicaments for treatment of tyrosine kinase-related diseases or disorders, and methods of treating tyrosine kinase-related diseases or disorders using these novel compounds, or pharmaceutically acceptable salts, solvates, prodrugs or compositions thereof.

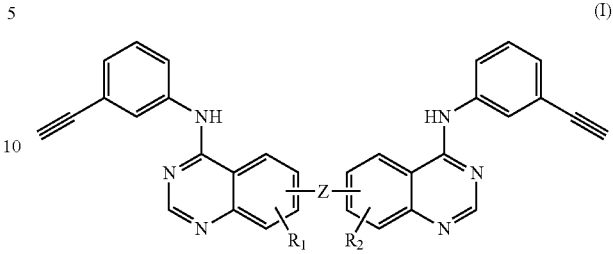

(I)

In one aspect the present invention provides compounds of formula (1):

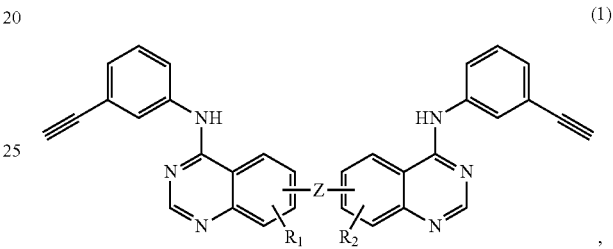

(1)

or a pharmaceutically acceptable salt, solvate, or prodrug thereof, wherein:

$R_1$ and $R_2$ are each independently —O-alkylene-OCH$_3$;

Z is a linker selected from the group consisting of: —O-(alkylene-$X_1$)$_m$-alkylene-($X_2$-alkylene)$_n$-O—, —O-(alkylene-$X_1$)$_m$-cycloalkylene-($X_2$-alkylene)$_n$-O—, and —O-(alkylene-$X_1$)$_m$-heterocyclylene-($X_2$-alkylene)$_n$-O—, wherein $X_1$ and $X_2$, at each occurrence, are independently —O—, —NR$_3$—, —S—, —SO—, or —SO$_2$—;

m and n, at each occurrence, are independently selected from integers 1 to 10;

$R_3$ is H, COR$_4$, or SO$_2$R$_4$; and $R_4$ is alkyl or cycloalkyl.

In another aspect, the present invention provides pharmaceutical compositions comprising any compound(s) of the present invention, alone or, optionally, in combination with a pharmaceutically acceptable carrier and/or one or more other agent(s).

In another aspect, the present invention provides methods of treating a patient suffering from tyrosine kinase-mediated diseases or disorders, comprising administering to a mammalian patient, for example, a human patient, in need thereof a therapeutically effective amount of a compound of the present invention, alone, or optionally, in combination with another compound of the present invention and/or at least one other type of therapeutic agent.

In another aspect, the present invention provides synthetic methods for preparing the tethered quinazoline derivative dimers.

These and other aspects or embodiments will become apparent from the following detailed description of the invention and claims.

DETAILED DESCRIPTION OF THE INVENTION

In one aspect the present invention provides a compound of formula (1):

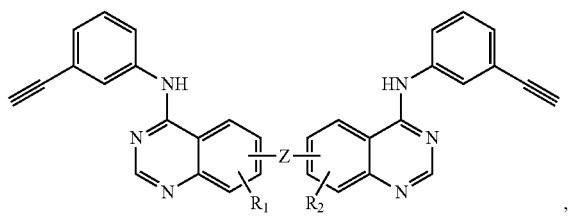

(1)

or a pharmaceutically acceptable salt, solvate, or prodrug thereof, wherein:
$R_1$ and $R_2$ are each independently —O-alkylene-OCH$_3$;
Z is a linker selected from the group consisting of: —O-(alkylene-X$_1$)$_m$-alkylene-(X$_2$-alkylene)$_n$-O—, —O-(alkylene-X$_1$)$_m$-cycloalkylene-(X$_2$-alkylene)$_n$-O—, and —O-(alkylene-X$_1$)$_m$-heterocyclylene-(X$_2$-alkylene)$_n$-O—;
$X_1$ and $X_2$, at each occurrence, are independently —O—, —NR$_3$—, —S—, —SO—, or —SO$_2$—;
m and n, at each occurrence, are independently selected from integers 1 to 10;
$R_3$ is H, COR$_4$, or SO$_2$R$_4$; and
$R_4$ is alkyl or cycloalkyl.

In one embodiment of this aspect, the invention provides a compound of formula (1), or a pharmaceutically acceptable salt, solvate, or prodrug thereof, wherein:
$R_1$ and $R_2$ are each independently —O-alkylene-OCH$_3$;
Z is a linker selected from the group consisting of: —O-(alkylene-O)$_m$-alkylene-(O-alkylene)$_n$-O—, —O-(alkylene-O)$_m$-cycloalkylene-(O-alkylene)$_n$-O—, and —O-(alkylene-O)$_m$-heterocyclylene-(O-alkylene-)$_n$-O—; and
m and n, at each occurrence, are independently selected from integers 1 to 10;

In another embodiment, the invention provides a compound of formula (1), or a pharmaceutically acceptable salt, solvate, or prodrug thereof, wherein:
$R_1$ and $R_2$ are each independently —O—(CH$_2$CH$_2$)$_m$—OCH$_3$, m=1, 2, or 3;
Z is a linker selected from the group consisting of: —O—(CH$_2$CH$_2$O)$_m$-alkylene-(OCH$_2$CH$_2$)$_n$—O—, —O—(CH$_2$CH$_2$O)$_m$-cycloalkylene-(OCH$_2$CH$_2$)$_n$—O—, and —O—(CH$_2$CH$_2$O)$_m$-heterocyclylene-(OCH$_2$CH$_2$)$_n$—O—; and
m and n, at each occurrence, are independently selected from integers from 1 to 10.

In another embodiment, the invention provides a compound of formula (1), or a pharmaceutically acceptable salt, solvate, or prodrug thereof, wherein:
$R_1$ and $R_2$ are each independently —O(CH$_2$CH$_2$)OCH$_3$;
Z is a linker selected from the group consisting of: —O—(CH$_2$CH$_2$O)$_m$—(CH$_2$)$_y$—(OCH$_2$CH$_2$)$_n$—O—, —O—(CH$_2$CH$_2$O)$_m$—(C$_3$-C$_{10}$)cycloalkylene-(OCH$_2$CH$_2$)$_n$—O—, —O—(CH$_2$CH$_2$O)$_m$-(3- to 10-membered)heterocyclylene-(OCH$_2$CH$_2$)$_n$—O—; and
m and n, at each occurrence, are independently selected from integers 1 to 10; and
y is an integer from 2 to 10.

In another embodiment, the invention provides a compound of formula (1), or a pharmaceutically acceptable salt, solvate, or prodrug thereof, wherein:
$R_1$ and $R_2$ are each independently —O(CH$_2$CH$_2$)OCH$_3$;
Z is a linker selected from the group consisting of: —O—(CH$_2$CH$_2$O)$_m$—CH$_2$CH$_2$—(OCH$_2$CH$_2$)$_n$—O—, —O—(CH$_2$CH$_2$O)$_m$—(C$_3$-C$_{10}$)cycloalkylene-(OCH$_2$CH$_2$)$_n$—O—, and —O—(CH$_2$CH$_2$O)$_m$-(3- to 10-membered)heterocyclylene-(OCH$_2$CH$_2$)$_n$—O—; and
m and n, at each occurrence, are independently selected from integers 1 to 10.

In any of the above embodiments, m and n are each preferably independently 1, 2, or 3, more preferably independently 1 or 2.

In one embodiment, which is applicable to any of the above embodiments, the linker Z connects position 6 on one quinazoline derivative moiety with position 6' on the other quinazoline derivative moiety in formula (1).

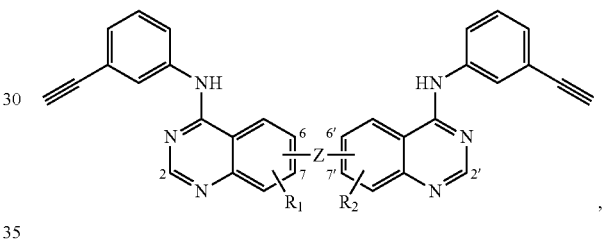

(1)

In another embodiment, which is applicable to any of the above embodiments, the linker Z connects position 7 on one quinazoline derivative moiety with position 7' on the other quinazoline derivative moiety in formula.

In another embodiment, which is applicable to any of the above embodiments, the linker Z cross-connects position 6 on one quinazoline derivative moiety with position 7' on the other quinazoline derivative moiety, or, vice versa, connects position 6' on one quinazoline derivative moiety with position 7 on the other quinazoline derivative moiety.

In another embodiment, which is applicable to any of the above embodiments, the two quinazoline derivative moieties are different (i.e., $R_1$ and $R_2$ are different).

In another embodiment, sometime preferred, which is applicable to any of the above embodiments, the two quinazoline derivative moieties are the same (i.e., $R_1$ and $R_2$ are the same).

In another embodiment, the present invention provides a compound selected from the group consisting of:

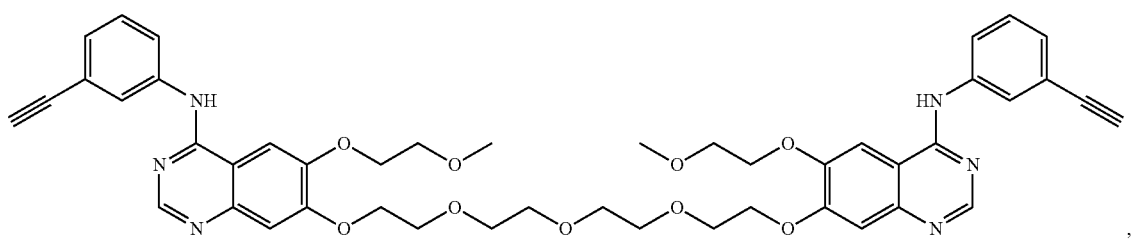

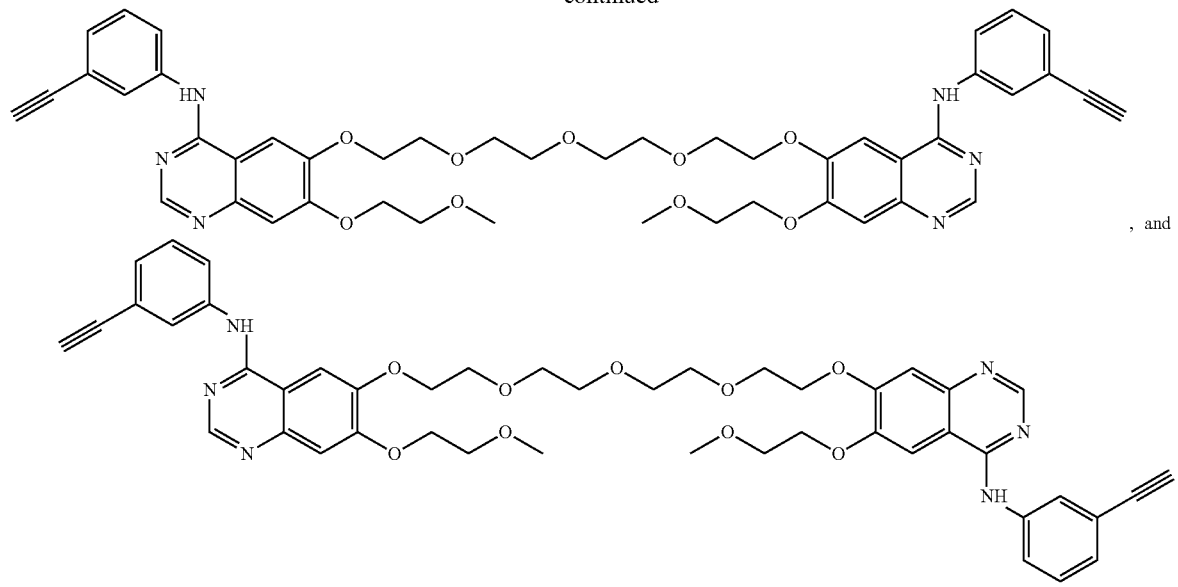

, and or a pharmaceutically acceptable salt, solvate, or prodrug thereof.

In a preferred embodiment, the present invention provides a compound of formula:

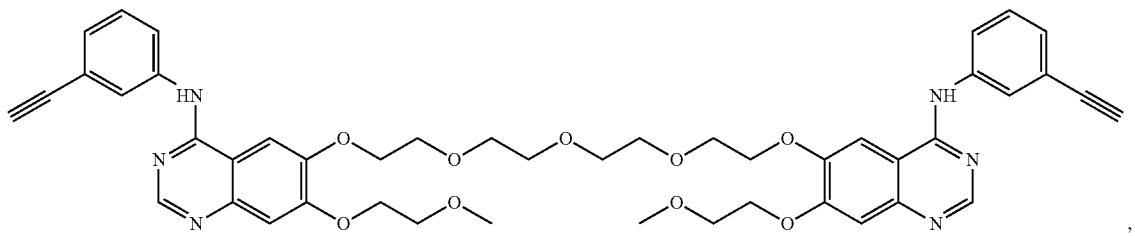 [SMILES: C#Cc1cccc(Nc2ncnc3cc(OCCOC)c(OCCOCCOCCOCCOc4cc5c(Nc6cccc(C#C)c6)ncnc5cc4OCCOC)cc23)c1]

, or pharmaceutically acceptable salt, solvate, or prodrug thereof.

In another aspect, the present invention provides a pharmaceutical composition comprising any of the compounds disclosed herein, or a pharmaceutically acceptable salt, solvate, or prodrug thereof, or a pharmaceutically acceptable salt thereof, and a pharmaceutically acceptable carrier.

This invention further relates to biological activity of a compound of the formula (1), in vitro and in vivo. Therefore, in another aspect, the present invention provides a method of treating a patient suffering from a tyrosine kinase-related disease or disorder, comprising administering to said patient a therapeutically effective amount of a compound of the present invention, or a pharmaceutically acceptable salt, solvate, or prodrug thereof, optionally and a pharmaceutically acceptable carrier.

In one embodiment of this aspect, the tyrosine kinase-related disease or disorder is selected from brain, lung, liver, bladder, chest, head and neck, esophagus, gastrointestinal tract, breast, ovary, cervix, and thyroid tumors, and complications associated therewith.

In another embodiment of this aspect, the tyrosine kinase-related disease or disorder is selected from the group consisting of lung cancer, brain cancer, kidney cancer, bone cancer, liver cancer, bladder cancer, breast, head and neck cancer, esophageal cancer, stomach cancer, colon cancer, rectum cancer, thyroid cancers, esophageal cancer, prostate cancer, and gynecological or angiogenesis, and combinations thereof.

In another embodiment of this aspect, the compound is administered at a dosage between 1 and 2,000 mg per day, in a single dose or in the form of individual doses for one to four times per day.

The compound of the present invention can be administered according to any methods known to those of skill in the art, including but not limited to oral administration in a dosage form selected from tablets, capsules, pills, powders, sustained release forms, solutions, suspensions; non-intestinal injection in a dosage form selected from sterile solutions, suspensions and emulsions; through local treatment in a dosage form selected from pastes, creams, and ointments; or via rectal administration in a dosage form of suppositories.

In a preferred embodiment of this aspect, the method comprises administering to a patient in need thereof a compound selected from the compounds exemplified in the examples, preferably Example 2, or a pharmaceutically acceptable salt, solvate, or prodrug thereof.

In any of the above embodiments of this aspect, the compound of the present invention can be administered alone or in combination with a second anti-cancer agent, including but not limited to erlotinib itself.

In another aspect, the present invention provides a method for preparing a compound of the formula (1):

(1)

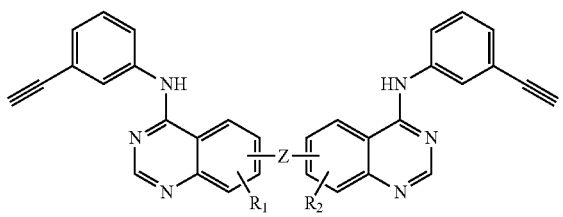

or a pharmaceutically acceptable salt or prodrug thereof, the method comprising the steps of:

1) reacting the compound of formula (6a) with an alkylating agent (e.g., of formula X—Z'—X) a to get the compound of formula (7):

(6a)

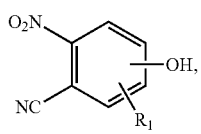

(7)

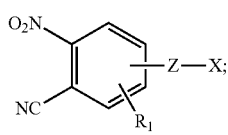

2) reacting the compound of formula (7) with the compound of formula (6b) to get the compound of formula (8):

(6b)

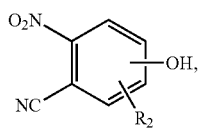

(8)

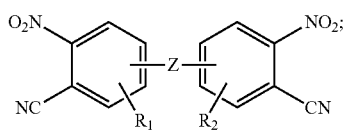

3) reducing the compound of formula (8) to get the compound of formula (9):

(9)

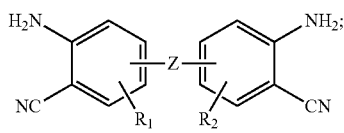

4) reacting the compound of formula (9) with DMF-DMA to get the compound of formula (10):

(10)

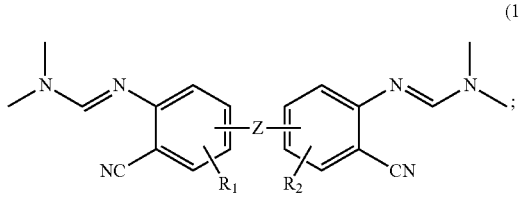

and 5) reacting the compound of formula (10) with 3-ethynyl-aniline to get the tethered quinazoline dimer compound of formula (1), wherein $R_1$, $R_2$, and Z take the definitions in any of the embodiments defined as above; and X—Z'—X is an alkylating agent, for example:
X-(alkylene-$X_1$)$_m$-alkylene-($X_2$-alkylene)$_n$-X, X-(alkylene-$X_1$)$_m$-cycloalkylene-($X_2$-alkylene)$_n$-X, or X-(alkylene-$X_1$)$_m$-heterocyclylene-($X_2$-alkylene)$_n$-X; wherein $X_1$ and $X_2$ are defined above; and X is a leaving group selected from halogen (e.g., Cl, Br, or I), methanesulfonate (MeSO$_3$—), and toluenesulfonate (TsO—).

When $R_1$ and $R_2$ are the same, the above steps 1) and 2) may be combined into one single step to obtain the compound of formula (8). By varying the positions of $R_1$, $R_2$, and —OH on the phenyl ring in compounds of formula (6a) and (6b), the connecting positions on the two quinazoline derivative moieties can be varied, e.g., between positions 6-6', 6-7', or 7-7' in formula (1) above. Conditions for the individual steps can be identified and optimized by those of skill in the art based on the present disclosure, as illustrated in the Examples below, in combination with the general literature in organic chemistry.

The starting materials (6a) and (6b) used for the synthesis of compound (1) may be synthesized by a method comprising the steps of:

a) reacting the compound of formula (2) with an alkylating agent of formula X-alkylene-O—CH$_3$, wherein X is a leaving group, for example, halide, methanesulfonate, toluenesulfonate, or the like, to get a compound of formula (3a) or (3b):

(2)

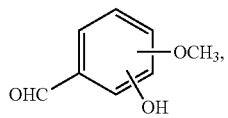

(3a)

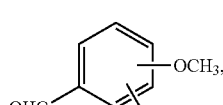

(3b)

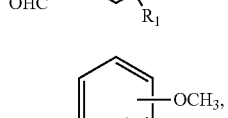

wherein $R_1$ and $R_2$ are each independently —O-alkylene-O—CH$_3$;

b) reacting the compound of formulae (3a) or (3b) with NH$_2$OH, or a salt thereof to give corresponding oxime adducts (—CH=NOH), followed by dehydrating the oxime adducts to get nitrile compounds of formula (4a) or (4b), respectively:

(4a)

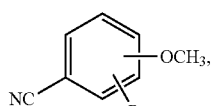

(4b)

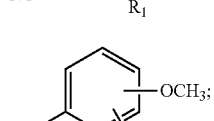

c) nitrating the compound of formula (4a) or (4b) using a nitrating agent to get the corresponding nitro-compound of formula (5a) or (5b), respectively:

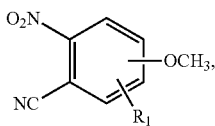

(5a)

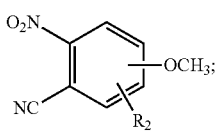

(5b)

and
d) selectively demethylating the compound of formula (5a) or (5b) to get the compound of formulae (6a) or (6b), respectively:

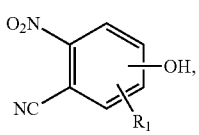

(6a)

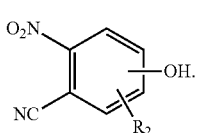

(6b)

As would be understood by those of skill in the art, by varying relative positions of $R_1$ and $R_2$ and —OH or —OCH$_3$ groups in the starting materials (2), (3a) or (3b), under controlled conditions, a variety of compounds (6a) and (6b) can be prepared based on the present disclosure.

Detailed conditions for the synthetic methods are further described in the following sections. Based on the present disclosure, in combination with routine general knowledge and practice in the field, a person of ordinary skill in the art would be able to synthesize any of the compounds described in the present application.

DEFINITIONS

As used herein, "alkyl" is intended to include both branched and straight-chain saturated aliphatic hydrocarbon groups containing 1 to 20 carbons, preferably 1 to 10 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. An alkyl group may optionally be substituted by 1 to 4 substituents independently selected from halo (for example F, Br, Cl, or I) haloalkyl (e.g., CF$_3$), alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain hydrocarbon radicals of 2 to 20 carbons, preferably 2 to 10 carbons, and more preferably 2 to 6 carbons, comprising at least one C=C bond.

Unless otherwise indicated, the term "alkynyl" as used herein by itself or as part of another group refers to straight or branched chain hydrocarbon radicals of 2 to 20 carbons, preferably 2 to 10 carbons, and more preferably 2 to 6 carbons, comprising at least one C≡C bond.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, more preferably one ring having 3 to 8 carbons, any of which groups may be optionally substituted with 1 to 4 substituents independently selected from the group consisting of halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl". For convenience, on occasions, the terms "alkyl" and "alkylene" may be used interchangeably in this application, as well as for other pairs, such as "cycloalkyl" and "cycloalkylene", or "heterocyclyl" and "heterocyclylene." These distinct monovalent and divalent groups are readily distinguishable to a person of ordinary skill in the art by considering the context in which these terms are used.

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example, CF$_3$, having the specified number of carbon atoms, substituted with one or more halogen (for example —C$_v$F$_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or heterocyclyl rings and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, hydroxy, nitro, cyano, amino, substituted amino and/or any of the substituents set out herein.

As used herein, the term "heterocyclyl", "heterocyclic system" or "heterocyclic ring" is intended to mean a stable 3- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

The term "heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano", as used herein, refers to a —CN group.
The term "nitro", as used herein, refers to an —NO$_2$ group.
The term "hydroxy" or "hydroxyl", as used herein, refers to an OH group.
The term "oxo", as used herein refers to an "=O" group.
Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, heterocyclyl, heterocyclylalkyl, cycloalkyl, cycloalkylalkyl, haloalkyl, hydroxyalkyl, alkoxyalkyl, or thioalkyl. These substituents may be further substituted.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis- and trans-geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young et al., *Antimicrobial Agents and Chemotherapy,* 2602-2605 (1995).

To the extent that compounds of the formula I, and salts thereof, may exist in their tautomeric form, all such tautomeric forms are contemplated herein as part of the present invention.

Unless otherwise specified, when any variable (e.g., $R_1$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$.

Also, combinations of substituents and/or variables are permissible only if such combinations result in stable compounds.

When a bond to a substituent is shown to cross a bond connecting two atoms in a ring, then such substituent may be bonded covalently to any available atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization. In addition, the compounds of formula I may exist in tautomeric form. Such tautomeric forms of the formula I are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit the activity of the enzyme 11-beta-hydroxysteroid dehydrogenase type I or effective to treat or prevent metabolic or other disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

Compounds of the present invention may be prepared as shown in the following reaction schemes and description thereof, as well as relevant literature procedures that may be used by one skilled in the art. Exemplary reagents and procedures for these reactions appear hereinafter and in the working Examples.

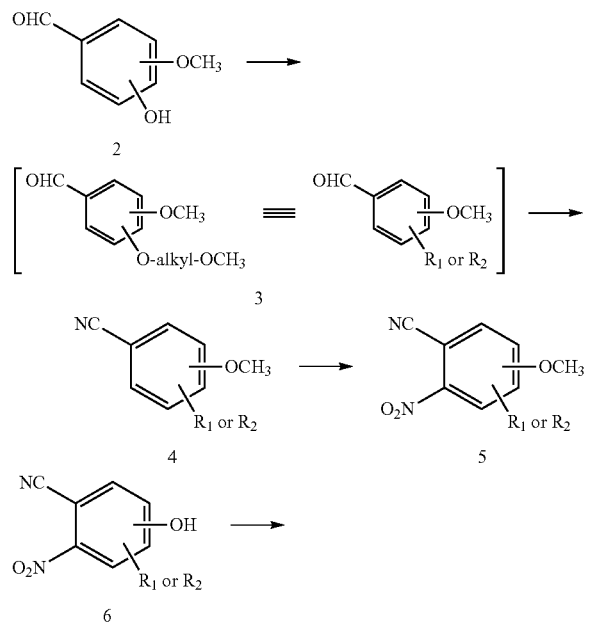

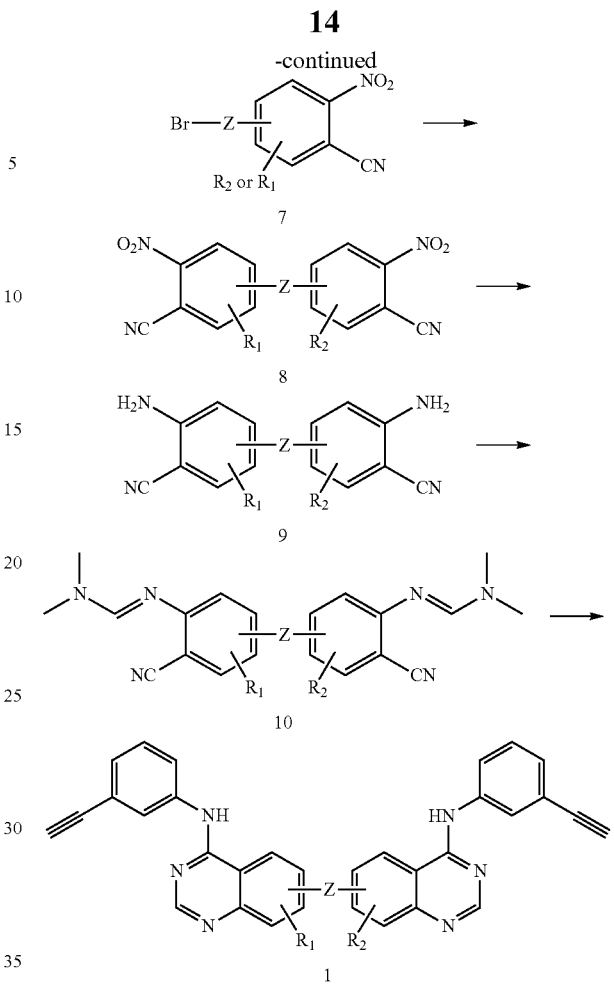

Reacting the compound of formula (2), a commercial available reagent with halogen-alkylene-OMe or MsO-alkylene-OMe or TsO-alkylene-OMe under basic condition to give compound of formula (3). Compound of formula (3) was treated with $NH_2OH.HCl$, and then dehydration to offer compound of formula (4). Nitrating the compound of formula (4) using a nitrating agent to get the compound of formula (5). De-methylation of compound with formula (5) using $AlCl_3$ to get the compound of formula (6). Reacting the compound of formula (6) with corresponding dibrominated long chains (e.g., $Br-(CH_2CH_2O)_m$-alkylene-$(OCH_2CH_2)_n-Br$) to get the compound of formula (7) or (8); reacting the compound of formula (6) with the compound of formula (7) to get the compound of formula (8). Reducing the compound of formula (8) using reductants such as zinc powder, or iron powder, or sodium hydrosulfite to get the compound of formula (9). Reacting the compound of formula (9) with N,N-dimethylformamide/N,N-dimethylacetylamide to get the compound of formula (10). Reacting the compound of formula (10) with 3-ethynylaniline to get the tethered quinazoline derivative dimers of formula (1).

ABBREVIATIONS

The following abbreviations are employed in the Examples and elsewhere herein:

Ph=phenyl
Bn=benzyl
i-Bu=iso-butyl

Me=methyl
Et=ethyl
Pr=propyl
Bu=butyl
Boc or BOC=tert-butoxycarbonyl
Cbz=carbobenzyloxy or carbobenzoxy or benzyloxycarbonyl
DCM=dichloromethane
DEAD=Diethyl azodicarboxylate
DIAD=Diisopropyl azodicarboxylate
DIEA=N,N-diisopropylethylamine
DMA=N,N-dimethylacetylamide
DMF=N,N-dimethylformamide
DMSO=dimethylsulfoxide
EtOAc=ethyl acetate
EDAC=3-ethyl-3'-(dimethylamino)propyl-carbodiimide hydrochloride (or 1-[(3-(dimethyl)amino)propyl])-3-ethyl-carbodiimide hydrochloride)
Fe=Iron
FMOC=fluorenylmethoxycarbonyl
HOAc or AcOH=acetic acid
HOAT=1-hydroxy-7-azabenzotriazole
HOBT=1-hydroxybenzotriazole
IPA=isopropyl alcohol or isopropanol
LAH=lithium aluminum hydride
mCPBA=3-Chloroperoxybenzoic acid
NMM=N-methyl morpholine
NBS=N-Bromosuccinimide
n-BuLi=n-butyllithium
Pd/C=palladium on carbon
$SOCl_2$=Thionyl chloride
TMS=trimethylsilyl
TEA=triethylamine
TFA=trifluoroacetic acid
THF=tetrahydrofuran
equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
TLC=thin layer chromatography
HPLC=high performance liquid chromatography
HPLC Rt=HPLC retention time
LC/MS=high performance liquid chromatography/mass spectrometry
MS or Mass Spec=mass spectrometry
NMR=nuclear magnetic resonance
mp=melting point
$K_3PO_4$=potassium phosphate
$Na_2SO_4$=sodium sulfate
$SiO_2$=silicon dioxide
EA=ethyl amine
$Et_2O$=diethyl ether
MeOH=methanol
$H_3PO_4$=phosphoric acid
$MgSO_4$=magnesium sulfate
Zn=Zinc
$ZnF_2$=Zinc Fluoride All chemicals were purchased from commercial suppliers and used without further purification. TLC was performed with Whatman 250-μm silica gel plates. Flash column chromatography was conducted with flash column silica gel (40-63 m) and column chromatography was conducted with standard silica gel. Nuclear magnetic resonance (NMR) spectra were recorded on a 400 MHz spectrometer with $Me_4Si$ as an internal standard (s=singlet, d=doublet, t=triplet, br=broad). Mass spectra (MS) were recorded on a mass spectrometer.

The formula (1) compounds, pharmaceutically acceptable salts and prodrugs thereof (hereafter the active compounds) may be prepared by any process known to be applicable to the preparation of chemically-related compounds.

A preferred embodiment of the present invention according to the scheme is described as follows:

In the first step, the compound of formula (2) is reacted with 2-chloro-methoxyethane in the presence of a base to get compound of formula (3). Temperature of the reaction is between 70-90° C., preferably 80° C. The base used in the reaction is selected from sodium or potassium hydroxide, carbonate, hydrogen carbonate. The solvent used in the reaction is DMF.

In the second step, the compound of formula (3) is reacted with $NH_2OH \cdot HCl$ in the presence of a base to form an oxime intermediate (—CHO changing into —CH=NOH), which undergoes dehydration to get the compound of formula (4). The temperature of the reaction is between 120-130° C., preferably 130° C. The base used in the reaction is selected from sodium acetate, potassium acetate, and the like. The solvent used in the reaction is acetic acid or the like.

In the third step, the compound of formula (4) is nitrated to get the compound of formula (5). The nitrating agent is selected from nitric acid, ammonium nitrate, and the like. The temperature of the reaction is between 0-60° C., preferably 25° C.

In the fourth step, the compound of formula (5) is demethylating using $AlCl_3$ to get the compound of formula (6). The amount of $AlCl_3$ used in the reaction is between 1 eq to 8 eq, preferably about 6 eq. The reaction time is varied between 1 h to 24 h, preferably about 1 h.

In the fifth step, the compound of formula (6) is reacted with corresponding dibrominated long chains of formula Br-alkylene-(O-alkylene)$_n$-Br in the presence of a base to get the compound of formula (7) or (8). Temperature of the reaction is between 70-90° C., preferably 80° C. The base used in the reaction is selected from sodium or potassium hydroxide, carbonate, hydrogen carbonate. The amount of dibrominated long chains used is between 0.3 eq to 5 eq. If less than 0.5 eq, the main product is the compound of formula (8); otherwise the main product is the compound of formula (7). The compound of formula (7) can react with the compound of formula (6) to get the compound of formula (8), under the same or similar conditions.

In the sixth step, the compound of formula (8) is reduced by a reductant to get the compound of formula (9). The reductant used in the reaction is selected from zinc powder, iron powder, and sodium hydrosulfite. Temperature of the reaction is between 70-130° C., preferably 78-90° C. Solvent used in the reaction is selected from water, ethanol, methanol, i-propanol, and acetic acid.

In the seventh step, the compound of formula (9) is reacted with DMF-DMA to get the compound of formula (10). Temperature of the reaction is between 90-105° C., preferably 100-104° C. The product can be isolated by adding ether, and used in next step without any purification. The reaction time is varied between 6 h to 24 h, preferably about 10 h.

In the eighth step, the compound of formula (10) is reacted with 3-ethynylaniline to get the erlotinib dimers. Temperature of the reaction is between 110-130° C., preferably 120-125° C. The reaction time is varied between 2 h to 5 h, preferably about 3 h. The crude product can be isolated by addition of ether.

The resulting dimers thus obtained are purified by recrystallization from different solvents such as ethyl acetate, acetonitrile, tetrahydrofuran, isopropyl alcohol, methanol, ethyl ether, acetone, water, or a mixture thereof, preferably ethyl ether or tetrahydrofuran.

Compounds prepared here were tested in the human lung adenocarcinoma epithelial cell line based assay. Those tested compounds have demonstrated lower, similar or superior in vitro activity in this assay as compared to that of Erlotinib tested in the same cell line. In particular, the compound of Example 2 showed higher activity than Erlotinib for the human lung adenocarcinoma epithelial cell line A549. Based on the methods of the present invention as disclosed herein, a person of ordinary skill in the art will be able to synthesize similar tethered bis-quinazoline derivatives, screen their activities, and obtain optimum compounds as drug candidates.

The details of the invention are given in the examples below which are provided to illustrate the invention only and therefore should not be construed to limit the scope of the present invention.

EXAMPLES

Example 1

Preparation of 7,7'-((((oxybis(ethane-2,1-diyl))bis(oxy))bis(ethane-2,1-diyl))bis(oxy))bis(N-(3-ethynylphenyl)-6-(2-methoxyethoxy)quinazolin-4-amine) ("Dimer 1")

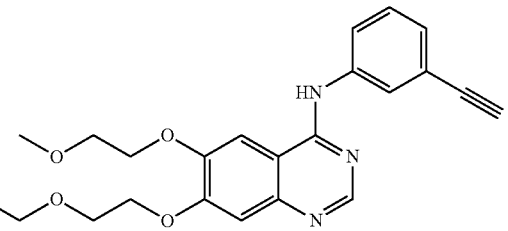

Preparation of 4-methoxy-3-(2-methoxyethoxy)benzaldehyde

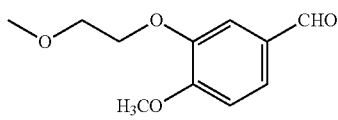

To a solution of 3-hydroxy-4-methoxybenzaldehyde (8.0 g) in DMF (60 mL) was added K$_2$CO$_3$ (8.0 g) and 1-chloro-2-methoxyethane (5.1 g). The resulting mixture was stirred at 80° C. overnight. After reaction finished, ethyl acetate (200 ml) was added, and washed with 2 N aqueous HCl solution, brine, dried over Na$_2$SO$_4$, filtered, concentrated. The residue was washed with petrol ether to give 4-methoxy-3-(2-methoxyethoxy)benzaldehyde (11 g) as a yellow solid. $^1$H-NMR (400 MHz, CDCl$_3$): δ: 9.84 (s, 1H); 7.49-7.43 (m, 2H); 6.98 (d, J=8.0, 1 H); 4.25-4.22 (m, 2H); 3.95 (s, 3H); 3.83-3.81 (m, 2H); 3.46 (s, 3H).

Preparation of 4-methoxy-3-(2-methoxyethoxy)benzonitrile

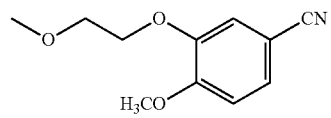

To a solution of 4-methoxy-3-(2-methoxyethoxy)benzaldehyde (10 g) in AcOH (80 mL) was added KOAc (9.5 g) and NH$_2$OH.HCl (6.7 g). The resulting mixture was heated at 130° C. for 18 h under N$_2$ atmospheres. After reaction finished, the mixture was poured into water (400 mL). The solid was collected, washed with water (100 mL) and air-dried to give 4-methoxy-3-(2-methoxyethoxy)benzonitrile (8.8 g) as a light yellow solid.

Preparation of 4-methoxy-5-(2-methoxyethoxy)-2-nitrobenzonitrile

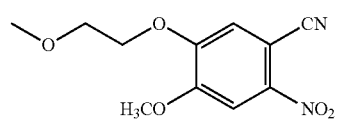

To a solution of 4-methoxy-3-(2-methoxyethoxy)benzonitrile (0.3 g) in TFAA (1.8 mL) and CHCl$_3$ (1.3 mL) was added NH$_4$NO$_3$ (0.135 g) portionwise. The resulting mixture was stirred at room temperature for 2 h. After reaction finished, the mixture was diluted with hexane and solid was collected. The solid was washed with hexane, H$_2$O, dilute NaHCO$_3$ solution, and then water again. This solid was air-dried to give 0.3 g of 4-methoxy-5-(2-methoxyethoxy)-2-nitrobenzonitrile. $^1$H-NMR (400 MHz, CDCl$_3$): δ: 7.79 (s, 1H), 7.27 (s, 1H), 4.31-4.28 (m, 2H), 4.02 (s, 1H), 3.85-3.82 (m, 2H), 3.46 (s, 3H).

Preparation of 4-hydroxy-5-(2-methoxyethoxy)-2-nitrobenzonitrile

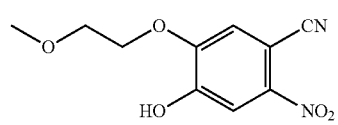

To a solution of 4-methoxy-5-(2-methoxyethoxy)-2-nitrobenzonitrile (1.5 g) in anhydrous DCM (30 mL) was added anhydrous AlCl$_3$ (6 g) at 0° C. The resulting mixture was heated to reflux for 1 h. After reaction finished, the mixture was diluted with 1N aqueous HCl (50 mL) and exacted with EA (3×50 mL). The combined organic layer was dried over Na$_2$SO$_4$, concentrated under reduced pressure, and purification by silica chromatography to give 0.8 g of 4-hydroxy-5-(2-methoxyethoxy)-2-nitrobenzonitrile.

Preparation of 4,4'-((((oxybis(ethane-2,1-diyl))bis(oxy))bis(ethane-2,1-diyl))bis(oxy))bis(5-(2-methoxyethoxy)-2-nitrobenzonitrile)

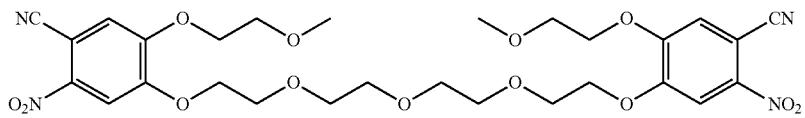 [SMILES: COCCOc1cc(C#N)c([N+](=O)[O-])cc1OCCOCCOCCOCCOc1cc([N+](=O)[O-])c(C#N)cc1OCCOC]

To a solution of 4-hydroxy-5-(2-methoxyethoxy)-2-nitrobenzonitrile. (0.25 g) in DMF (5 mL) was added 1-bromo-2-(2-(2-(2-bromoethoxy) ethoxy)ethoxy)ethane (0.15 g) and $K_2CO_3$ (0.3 g). The resulting mixture was heated at 80° C. overnight under $N_2$ atmospheres. After reaction finished, the mixture was diluted with water (50 mL) and exacted with EA (3×50 mL). The combined organic layer was dried over $Na_2SO_4$, concentrated under reduced pressure, and purification by silica chromatography to give 0.3 g 4,4'-((((oxybis(ethane-2,1-diyl))-bis(oxy))bis(ethane-2,1-diyl))-bis(oxy))bis-(5-(2-methoxyethoxy)-2-nitrobenzonitrile). $^1$H-NMR (400 MHz, $CDCl_3$): δ: 7.92 (s, 2H), 7.26 (s, 2H), 4.36-4.27 (m, 8H), 3.92-3.90 (m, 4H), 3.83-3.81 (m, 4H), 3.70-3.69 (m, 4H), 3.65-3.63 (m, 4H), 3.45 (s, 6H).

Preparation of 4,4'-((((oxybis(ethane-2,1-diyl))bis(oxy))bis(ethane-2,1-diyl))bis(oxy))bis(2-amino-5-(2-methoxyethoxy)benzonitrile)

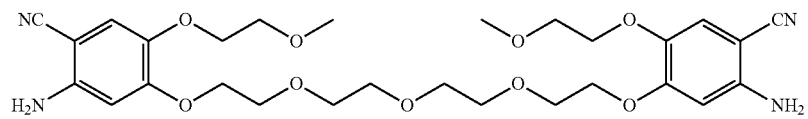

To a solution of 4,4'-((((oxybis(ethane-2,1-diyl))bis(oxy))bis(ethane-2,1-diyl))-bis(oxy))bis(5-(2-methoxyethoxy)-2-nitrobenzonitrile) (0.3 g) in AcOH (10 mL) and i-PrOH (10 mL) was added iron powder (0.75 g). The resulting mixture was heated to reflux for 1 h. After reaction finished, the mixture was cooled to room temperature, filtered, the precipitate washed with EA (10 mL). The combined washings and filtrate were concentrated under reduced pressure and purification by silica chromatography to give 0.22 g of 4,4'-((((oxybis(ethane-2,1-diyl))bis(oxy))bis(ethane-2,1-diyl))-bis(oxy))bis(2-amino-5-(2-methoxyethoxy)benzonitrile).
$^1$H-NMR (400 MHz, $CDCl_3$): δ: 6.88 (s, 2H), 6.33 (s, 2H), 4.28 (br, 4H), 4.15-4.12 (m, 4H), 4.05-4.02 (m, 4H), 3.86-3.83 (m, 4H), 3.72-3.68 (m, 8H), 3.66-3.64 (m, 4H), 3.42 (s, 6H).

Preparation of (1E,1'E)-N',N'''-(((((oxybis(ethane-2,1-diyl))bis(oxy))bis(ethane-2,1-diyl))-bis(oxy))bis(2-cyano-4-(2-methoxyethoxy)-5,1-phenylene))bis(N,N-dimethylformimidamide)

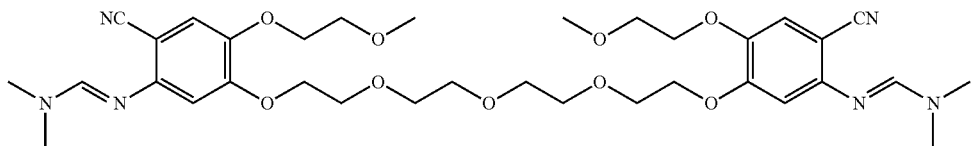

4,4'-((((oxybis(ethane-2,1-diyl))bis(oxy))bis(ethane-2,1-diyl))bis(oxy))bis(2-amino-5-(2-methoxyethoxy)benzonitrile) (0.2 g) was added to DMF-DMA (3 mL), the resulting mixture was heated to reflux overnight under N₂ atmospheres. After reaction finished, the mixture was diluted with Et₂O (30 mL) and solid was collected. The solid was washed with Et₂O and air-dried to give (1E,1'E)-N',N''-(((((oxybis(ethane-2,1-diyl))bis(oxy))bis(ethane-2,1-diyl))bis(oxy))bis(2-cyano-4-(2-methoxyethoxy)-5,1-phenylene))bis(N,N-dimethylformimidamide) (0.2 g) as a yellow solid, which used in next step directly without any purification.

Preparation of 7,7'-((((oxybis(ethane-2,1-diyl))bis(oxy))bis(ethane-2,1-diyl))bis(oxy))bis(N-(3-ethynylphenyl)-6-(2-methoxyethoxy)quinazolin-4-amine) (Dimer 1)

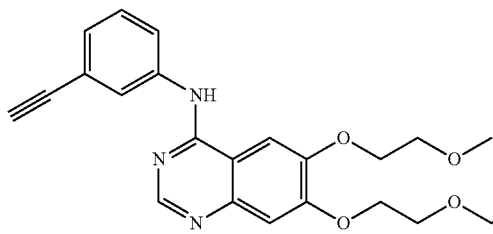

(1E,1'E)-N',N''-(((((oxybis(ethane-2,1-diyl))bis(oxy))bis(ethane-2,1-diyl))bis(oxy))bis(2-cyano-4-(2-methoxyethoxy)-5,1-phenylene))bis(N,N-dimethylformimidamide) (0.2 g), 3-ethynylaniline (0.13 g) were added to AcOH (5 mL), the resulting mixture was heated at reflux for 3 h under N₂ atmospheres. After reaction finished, the mixture was diluted with Et₂O (30 mL) and solid was collected. The solid was washed with Et₂O and air-dried to give 7,7'-((((oxybis(ethane-2,1-diyl))bis(oxy))bis(ethane-2,1-diyl))-bis(oxy))-bis(N-(3-ethynylphenyl)-6-(2-methoxyethoxy)quinazolin-4-amine) (0.12 g, dimer 1) as a brown solid. ¹H-NMR (400 MHz, DMSO-d₆): δ: 9.47 (br, 2H), 8.48 (s, 2H), 7.99 (s, 2H), 7.89 (d, J=8.0, 2 H), 7.84 (s, 2H), 7.42-7.38 (m, 2H), 7.22-7.19 (m, 4H), 4.35-4.25 (m, 8H), 4.20 (s, 2H), 3.88-3.70 (m, 8H), 3.66-3.55 (m, 8H), 3.36 (s, 6H).

Example 2

Preparation of 6,6'-((((oxybis(ethane-2,1-diyl))bis(oxy))bis(ethane-2,1-diyl))bis(oxy))bis(N-(3-ethynylphenyl)-7-(2-methoxyethoxy)quinazolin-4-amine) ("Dimer 2")

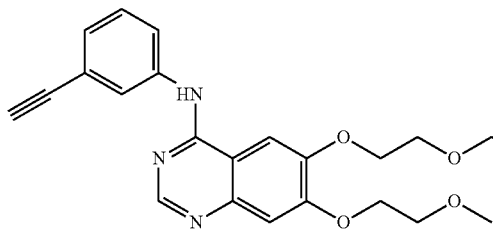

Preparation of 3-methoxy-4-(2-methoxyethoxy)benzaldehyde

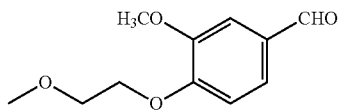

To a solution of 3-methoxy-4-hydroxybenzaldehyde (8.0 g) in DMF (60 mL) was added K₂CO₃ (8.0 g) and 1-chloro-2-methoxyethane (5.1 g). The resulting mixture was stirred at 80° C. overnight. After reaction finished, ethyl acetate (200 mL) was added, and washed with 2 N aqueous HCl solution, brine, dried over Na₂SO₄, filtered, concentrated. The residue was washed with petrol ether to give 3-methoxy-4-(2-methoxyethoxy)benzaldehyde (10 g) as a yellow solid. ¹H-NMR (400 MHz, CDCl₃): δ: 9.86 (s, 1H); 7.45-7.41 (m, 2H); 7.01 (d, J=8.0, 1H); 4.27-4.25 (m, 2H); 3.93 (s, 3H); 3.85-3.82 (m, 2H); 3.46 (s, 3H).

Preparation of 3-methoxy-4-(2-methoxyethoxy)benzonitrile

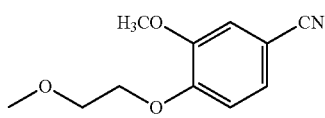

To a solution of 3-methoxy-4-(2-methoxyethoxy)benzaldehyde (10 g) in AcOH (80 mL) was added KOAc (9.5 g) and NH₂OH.HCl (6.7 g). The resulting mixture was heated at 130° C. for 18 h under N₂ atmospheres. After reaction finished, the mixture was poured into water (400 mL). The solid was collected, washed with water (100 mL) and air-dried to give 3-methoxy-4-(2-methoxyethoxy)benzonitrile (9 g) as a light yellow solid. ¹H-NMR (400 MHz, CDCl₃): δ: 7.26 (dd, J=8.4, 1.6, 1H), 7.08 (d, J=1.6, 1H), 6.93 (d, J=8.4, 1H), 4.23-4.20 (m, 2H), 3.88 (s, 3H), 3.82-3.80 (m, 2H), 3.45 (s, 3H).

Preparation of
5-methoxy-4-(2-methoxyethoxy)-2-nitrobenzonitrile

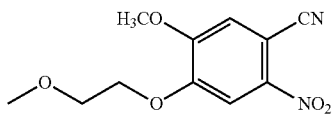 [SMILES: COCCOc1cc([N+](=O)[O-])c(C#N)cc1OC]

To a solution of 3-methoxy-4-(2-methoxyethoxy)benzonitrile (0.3 g) in TFAA (1.8 mL) and CHCl$_3$ (1.3 ml) was added NH$_4$NO$_3$ (0.135 g) portionwise. The resulting mixture was stirred at room temperature for 2 h. After reaction finished, the mixture was diluted with hexane and solid was collected. The solid was washed with hexane, H$_2$O, dilute NaHCO$_3$ solution, and then water again. This solid was air-dried to give 0.31 g of 5-methoxy-4-(2-methoxyethoxy)-2-nitrobenzonitrile. $^1$H-NMR (400 MHz, CDCl$_3$): δ: 7.85 (s, 1H), 7.20 (s, 1H), 4.35-4.29 (m, 2H), 4.02 (s, 1H), 3.88-3.83 (m, 2H), 3.47 (s, 3H).

Preparation of
5-hydroxy-4-(2-methoxyethoxy)-2-nitrobenzonitrile

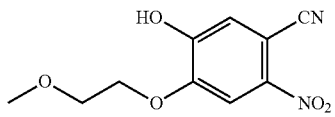 [SMILES: COCCOc1cc([N+](=O)[O-])c(C#N)cc1O]

To a solution of 5-methoxy-4-(2-methoxyethoxy)-2-nitrobenzonitrile (1.5 g) in anhydrous DCM (30 mL) was added anhydrous AlCl$_3$ (6 g) at 0° C. The resulting mixture was heated to reflux for 1 h. After reaction finished, the mixture was diluted with 1N aqueous HCl (50 mL) and exacted with EA (3×50 mL). The combined organic layer was dried over Na$_2$SO$_4$, concentrated under reduced pressure, and purification by silica chromatography to give 0.5 g of 5-hydroxy-4-(2-methoxyethoxy)-2-nitrobenzonitrile. $^1$H-NMR (400 MHz, CDCl$_3$): δ: 7.85 (s, 1H), 7.33 (s, 1H), 4.32-4.30 (m, 2H), 3.87-3.84 (m, 2H), 3.50 (s, 3H).

Preparation of 5,5'-((((oxybis(ethane-2,1-diyl))bis(oxy))bis(ethane-2,1-diyl))bis(oxy))bis(4-(2-methoxyethoxy)-2-nitrobenzonitrile)

To a solution of 5-hydroxy-4-(2-methoxyethoxy)-2-nitrobenzonitrile (0.42 g) in DMF (5 mL) was added 1-bromo-2-(2-(2-(2-bromoethoxy)ethoxy)ethoxy)ethane (0.26 g) and K2CO3 (0.5 g). The resulting mixture was heated at 80° C. overnight under N$_2$ atmospheres. After reaction finished, the mixture was diluted with water (50 mL) and exacted with EA (3×50 mL). The combined organic layer was dried over Na$_2$SO$_4$, concentrated under reduced pressure, and purification by silica chromatography to give 0.25 g of 5,5'-((((oxybis(ethane-2,1-diyl))bis(oxy))bis(ethane-2,1-diyl))-bis(oxy))bis(4-(2-methoxyethoxy)-2-nitrobenzonitrile). $^1$H-NMR (400 MHz, CDCl$_3$): δ: 7.84 (s, 2H), 7.35 (s, 2H), 4.33-4.28 (m, 8H), 3.92-3.90 (m, 4H), 3.83-3.81 (m, 4H), 3.73-3.70 (m, 4H), 3.68-3.65 (m, 4H), 3.45 (s, 6H).

Preparation of 5,5'-((((oxybis(ethane-2,1-diyl))bis(oxy))bis(ethane-2,1-diyl))bis(oxy))bis(2-amino-4-(2-methoxyethoxy)benzonitrile)

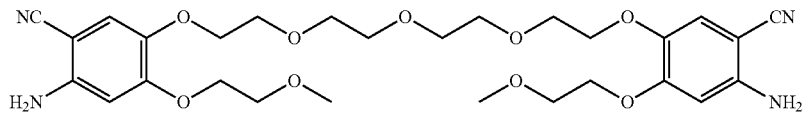

To a solution of 5,5'-((((oxybis(ethane-2,1-diyl))bis(oxy))bis(ethane-2,1-diyl))bis(oxy))bis(4-(2-methoxyethoxy)-2-nitrobenzonitrile) (0.2 g) in AcOH (10 mL) and i-PrOH (10 mL) was added iron powder (0.5 g). The resulting mixture was heated to reflux for 1 h. After reaction finished, the mixture was cooled to room temperature, filtered, the precipitate washed with EA (10 mL). The combined washings and filtrate were concentrated under reduced pressure and purification by silica chromatography to give 0.15 g of 5,5'-((((oxy-bis(ethane-2,1-diyl))bis(oxy))bis(ethane-2,1-diyl))bis(oxy))bis(2-amino-4-(2-methoxyethoxy)benzonitrile). $^1$H-NMR (400 MHz, CDCl$_3$): δ: 6.90 (s, 2H), 6.25 (s, 2H), 4.20-4.16 (br, 4H), 4.15-4.02 (m, 8H), 3.82-3.79 (m, 4H), 3.77-3.75 (m, 4H), 3.72-3.70 (m, 4H), 3.68-3.66 (m, 4H), 3.43 (s, 6H).

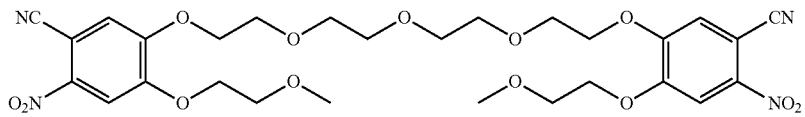 [SMILES: COCCOc1cc([N+](=O)[O-])c(C#N)cc1OCCOCCOCCOCCOc1cc(C#N)c([N+](=O)[O-])cc1OCCOC]

Preparation of (1E,1'E)-N',N''-(((((oxybis(ethane-2,1-diyl))bis(oxy))bis(ethane-2,1-diyl))bis(oxy))bis(2-cyano-5-(2-methoxyethoxy)-4,1-phenylene))bis(N,N-dimethylformimidamide)

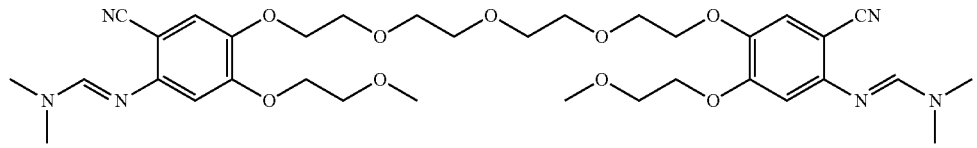

5,5'-((((oxybis(ethane-2,1-diyl))bis(oxy))bis(ethane-2,1-diyl))bis(oxy))bis(2-amino-4-(2-methoxyethoxy)benzonitrile) (0.15 g) was added to DMF-DMA (3 mL), the resulting mixture was heated to reflux overnight under N₂ atmospheres. After reaction finished, the mixture was diluted with Et₂O (30 mL) and solid was collected. The solid was washed with Et₂O and air-dried to give (1E,1'E)-N',N''-(((((oxybis(ethane-2,1-diyl))bis(oxy))bis(ethane-2,1-diyl))bis(oxy))bis(2-cyano-5-(2-methoxyethoxy)-4,1-phenylene))bis(N,N-dimethylformimidamide) (0.15 g) as a yellow solid, which used in next step directly without any purification.

Preparation of 6,6'-(2,2'-(2,2'-oxybis(ethane-2,1-diyl)bis(oxy))bis(ethane-2,1-diyl))bis(oxy)bis(N-(3-ethynylphenyl)-7-(2-methoxyethoxy)quinazolin-4-amine) ("Dimer 2")

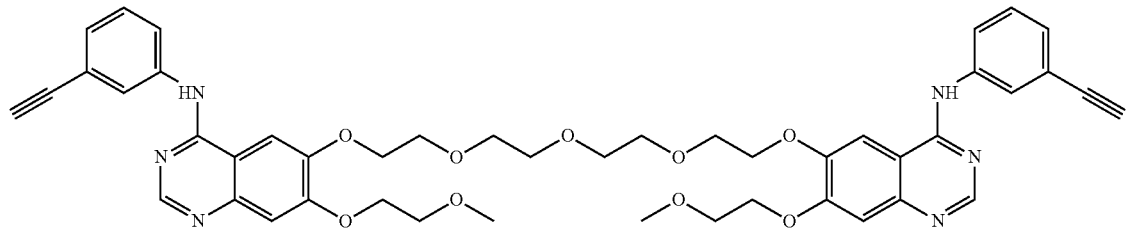 [SMILES: C#Cc1cccc(Nc2ncnc3cc(OCCOC)c(OCCOCCOCCOCCOc4cc5c(Nc6cccc(C#C)c6)ncnc5cc4OCCOC)cc23)c1]

(1E,1'E)-N',N''-(((((oxybis(ethane-2,1-diyl))bis(oxy))bis(ethane-2,1-diyl))bis(oxy))bis(2-cyano-5-(2-methoxyethoxy)-4,1-phenylene))bis(N,N-dimethylformimidamide) (0.15 g), 3-ethynylaniline (0.1 g) were added to AcOH (5 mL), the resulting mixture was heated at reflux for 3 h under N₂ atmospheres. After reaction finished, the mixture was diluted with Et₂O (30 mL) and solid was collected. The solid was washed with Et₂O and air-dried to give 6,6'-(((((oxybis(ethane-2,1-diyl))bis(oxy))bis(ethane-2,1-diyl))bis(oxy))-bis(N-(3-ethynylphenyl)-7-(2-methoxyethoxy)-quinazolin-4-amine) (0.12 g, dimer 2) as a brown solid. $^1$H-NMR (400 MHz, CDCl₃): δ: 8.78 (br, 2H), 8.62 (s, 2H), 7.96 (s, 2H), 7.84 (d, J=8.0, 2H), 7.55 (s, 2H), 7.33-7.29 (m, 2H), 7.23 (d, J=7.6, 2H), 7.04 (s, 2H), 4.07-4.04 (m, 4H), 4.00-3.97 (m, 4H), 3.71-3.63 (m, 16H), 3.62 (s, 6H), 3.07 (s, 2H).

Example-3

Preparation of N-(3-ethynylphenyl)-6-(2-(2-(2-(2-((4-((3-ethynylphenyl)amino)-6-(2-methoxyethoxy)quinazolin-7-yl)oxy)ethoxy)ethoxy)ethoxy)ethoxy)-7-(2-methoxyethoxy)quinazolin-4-amine ("Dimer 3")

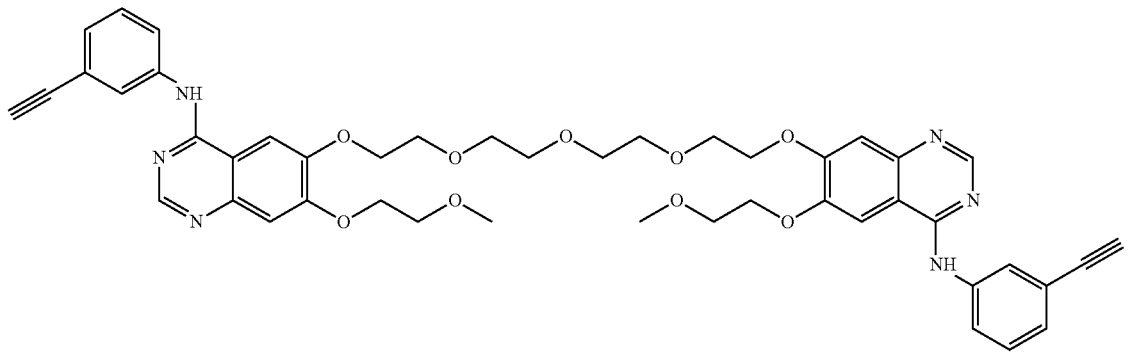 [SMILES: C#Cc1cccc(Nc2ncnc3cc(OCCOCCOCCOCCOc4cc5c(Nc6cccc(C#C)c6)ncnc5cc4OCCOC)c(OCCOC)cc23)c1]

Preparation of 5-(2-(2-(2-(2-bromoethoxy)ethoxy)ethoxy)ethoxy)-4-(2-methoxyethoxy)-2-nitrobenzonitrile

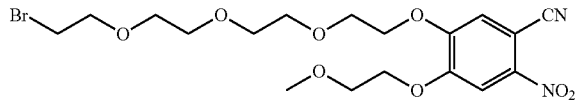 [SMILES: COCCOc1cc([N+](=O)[O-])c(C#N)cc1OCCOCCOCCOCCBr]

To a solution of 5-hydroxy-4-(2-methoxyethoxy)-2-nitrobenzonitrile (0.4 g) in DMF (8 mL) was added 1-bromo-2-(2-(2-(2-bromoethoxy)ethoxy)ethoxy)ethane (1.0 g) and $K_2CO_3$ (0.5 g). The resulting mixture was heated at 80° C. overnight under $N_2$ atmospheres. After reaction finished, the mixture was diluted with water (50 mL) and exacted with EA (3×50 mL). The combined organic layer was dried over $Na_2SO_4$, concentrated under reduced pressure, and purification by silica chromatography to give 0.2 g of 5-(2-(2-(2-(2-bromoethoxy)ethoxy)ethoxy)ethoxy)-4-(2-methoxyethoxy)-2-nitrobenzonitrile. $^1$H-NMR (400 MHz, $CDCl_3$): δ: 7.85 (s, 1H), 7.33 (s, 1H), 4.33-4.28 (m, 4H), 3.95-3.92 (m, 2H), 3.83-3.79 (m, 4H), 3.74-3.72 (m, 2H), 3.69-3.66 (m, 6H), 3.49-3.47 (m, 2H), 3.45 (s, 3H).

Preparation of 4-(2-(2-(2-(2-(5-cyano-2-(2-methoxyethoxy)-4-nitrophenoxy)ethoxy)ethoxy)ethoxy)ethoxy)-5-(2-methoxyethoxy)-2-nitrobenzonitrile

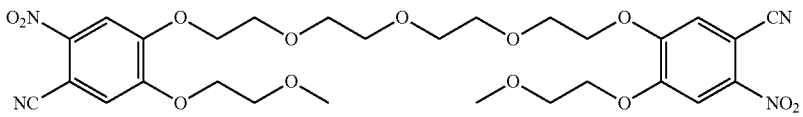 [SMILES: COCCOc1cc(C#N)c(N)cc1OCCOCCOCCOCCOc1cc(C#N)c(N)cc1OCCOC]

To a solution of 5-(2-(2-(2-(2-bromoethoxy)ethoxy)ethoxy)ethoxy)-4-(2-methoxyethoxy)-2-nitrobenzonitrile (0.2 g) in DMF (8 mL) was added 4-hydroxy-5-(2-methoxyethoxy)-2-nitrobenzonitrile (0.1 g) and $K_2CO_3$ (0.5 g). The resulting mixture was heated at 80° C. overnight under $N_2$ atmospheres. After reaction finished, the mixture was diluted with water (50 mL) and exacted with EA (3×50 mL). The combined organic layer was dried over $Na_2SO_4$, concentrated under reduced pressure, and purification by silica chromatography to give 0.2 g of 4-(2-(2-(2-(2-(5-cyano-2-(2-methoxyethoxy)-4-nitrophenoxy)ethoxy)ethoxy)ethoxy)ethoxy)-5-(2-methoxyethoxy)-2-nitrobenzonitrile. $^1$H-NMR (400 MHz, $CDCl_3$): δ: 7.92 (s, 1H), 7.84 (s, 1H), 7.35 (s, 1H), 7.26 (s, 1H), 4.35-4.25 (m, 8H), 3.95-3.89 (m, 4H), 3.85-3.78 (m, 4H), 3.77-3.63 (m, 8H), 3.45 (s, 6H).

Preparation of 2-amino-5-(2-(2-(2-(2-(5-amino-4-cyano-2-(2-methoxyethoxy)phenoxy)ethoxy)ethoxy)ethoxy)ethoxy)-4-(2-methoxyethoxy)benzonitrile

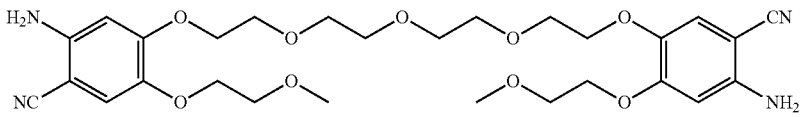

To a solution of 4-(2-(2-(2-(2-(5-cyano-2-(2-methoxyethoxy)-4-nitrophenoxy)ethoxy)ethoxy)ethoxy)ethoxy)-5-(2-methoxyethoxy)-2-nitrobenzonitrile (0.2 g) in AcOH (10 mL) and i-PrOH (10 mL) was added iron powder (0.5 g). The resulting mixture was heated to reflux for 1 h. After reaction finished, the mixture was cooled to room temperature, filtered, the precipitate washed with EA (10 mL). The combined washings and filtrate were concentrated under reduced pressure and purification by silica chromatography to give 0.18 g of 2-amino-5-(2-(2-(2-(2-(5-amino-4-cyano-2-(2-methoxyethoxy)phenoxy)ethoxy)ethoxy)ethoxy)ethoxy)-4-(2-methoxyethoxy)benzonitrile. $^1$H-NMR (400 MHz, $CDCl_3$): δ: 6.91 (s, 1H), 6.88 (s, 1H), 6.34 (s, 1H), 6.25 (s, 1H), 4.30 (br, 2H), 4.22-4.05 (m, 10H), 3.88-3.65 (m, 16H), 3.43 (s, 6H).

Preparation of (E)-N-(2-cyano-4-(2-(2-(2-(2-(4-cyano-5-((E)-((dimethylamino)methylene)amino)-2-(2-methoxyethoxy)phenoxy)ethoxy)ethoxy)ethoxy)ethoxy)-5-(2-methoxyethoxy)phenyl)-N,N-dimethylformimidamide

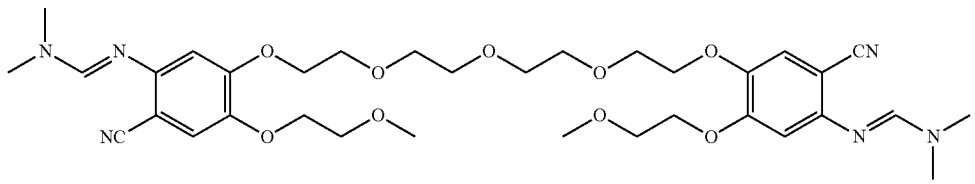

2-Amino-5-(2-(2-(2-(2-(5-amino-4-cyano-2-(2-methoxyethoxy)phenoxy)ethoxy)ethoxy)ethoxy)ethoxy)-4-(2-methoxyethoxy)benzonitrile (0.18 g) was added to DMF-DMA (3 mL), the resulting mixture was heated to reflux overnight under N₂ atmospheres. After reaction finished, the mixture was diluted with Et₂O (30 mL) and solid was collected. The solid was washed with Et₂O and air-dried to give (E)-N'-(2-cyano-4-(2-(2-(2-(2-(4-cyano-5-((E)-((dimethylamino)methylene)amino)-2-(2-methoxyethoxy)phenoxy)ethoxy)ethoxy)ethoxy)ethoxy)-5-(2-methoxyethoxy)phenyl)-N,N-dimethylformimidamide (0.2 g) as a yellow solid, which was used in next step directly without any purification.

Preparation of N-(3-ethynylphenyl)-6-(2-(2-(2-(2-((4-((3-ethynylphenyl)amino)-6-(2-methoxyethoxy)quinazolin-7-yl)oxy)ethoxy)ethoxy)ethoxy)ethoxy)-7-(2-methoxyethoxy)quinazolin-4-amine (Dimer 3)

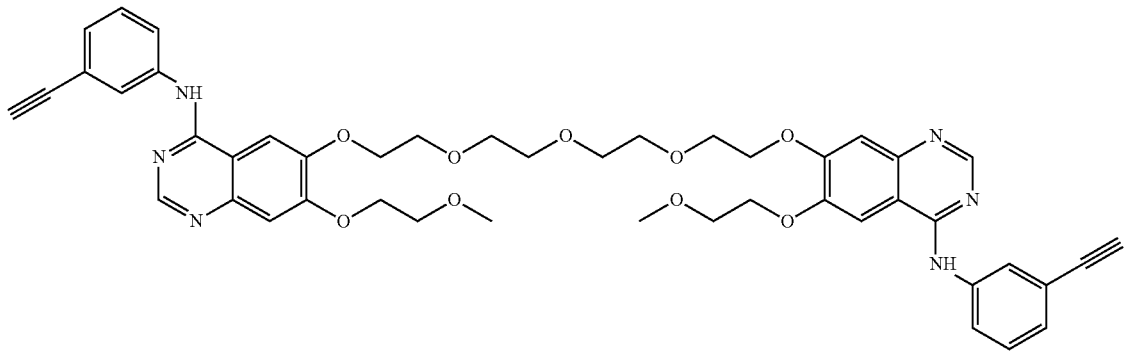

(E)-N'-(2-cyano-4-(2-(2-(2-(2-(4-cyano-5-((E)-((dimethylamino)methylene)amino)-2-(2-methoxyethoxy)phenoxy)ethoxy)ethoxy)ethoxy)ethoxy)-5-(2-methoxyethoxy)phenyl)-N,N-dimethylformimidamide (0.2 g), 3-ethynylaniline (0.11 g) were added to AcOH (5 mL), the resulting mixture was heated at reflux for 3 h under N₂ atmospheres. After reaction finished, the mixture was diluted with Et₂O (30 ml) and solid was collected. The solid was washed with Et₂O and air-dried to give N-(3-ethynylphenyl)-6-(2-(2-(2-(2-((4-((3-ethynylphenyl)-amino)-6-(2-methoxyethoxy)quinazolin-7-yl)-oxy)ethoxy)ethoxy)ethoxy)ethoxy)-7-(2-methoxyethoxy)quinazolin-4-amine (0.14 g, dimer 3) as a brown solid. $^1$H-NMR (400 MHz, DMSO-d₆): δ: 9.46 (br, 2H), 8.48 (s, 2H), 7.98 (s, 2H), 7.89-7.83 (m, 4H), 7.40-7.37 (m, 2H), 7.22-7.19 (m, 4H), 4.33-4.25 (m, 8H), 4.21 (s, 1H), 4.20 (s, 1H), 3.90-3.80 (m, 4H), 3.80-3.70 (m, 4H), 370-7.60 (m, 4H), 3.60-3.50 (m, 4H), 3.35 (s, 3H), 3.34 (s, 3H).

Biologic Assay

Growth Inhibition In Vitro of Human Tumor Cell Line A549 by Examples:

Human lung adenocarcinoma epithelial cell line A549 was obtained from American Type Culture Collection (ATCC) and maintained in Dulbecco modified eagle medium supplemented with 10% fetal bovine serum. MTT assay was performed using the MTT cell proliferation assay kit (ATCC). Briefly, 3×103 A549 cells/well were plated in 96 well plates overnight and then incubated with different concentrations of tested compounds or vehicle controls for 24 hours. Ten μl of MTT reagent was added to each well for 120 min. The formazan crystal was dissolved with MTT detergent, and the OD value was measured at 570 nm using a SpectraMax M3 microplate reader (Molecular Devices). Data were normalized to vehicle controls and processed using GraphPad Prism 5.00.

TABLE 1

| Tumor cell growth inhibition of examples in human tumor cell line A549 | | | | |
|---|---|---|---|---|
| Compound | Erlotinib | dimer 2 | dimer 1 | dimer 3 |
| IC 50 (μM) | 9.9 | 5.1 | >80 | >80 |

UTILITIES AND COMBINATIONS

The compounds of the present invention, especially the compound of Example 2 or the like, possess activity as inhibitors of epidermal growth factor receptor (EGFR) tyrosine kinase, and, therefore, may be used in the treatment of diseases associated with epidermal growth factor receptor (EGFR) tyrosine kinase mediated disorder. Accordingly, the compounds of the present invention can be administered to mammals, preferably humans, for the treatment of a variety of conditions and disorders associated with epidermal growth factor receptor (EGFR) tyrosine kinase. In a preferred embodiment, the method relates to the treatment of cancer such as brain, lung, squamous cell, bladder, gastric, pancreatic, breast, head, neck, oesophageal, prostate, colorectal, gynecological or thyroid cancer.

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an anticancer agent or other pharmaceutically active material.

The pharmaceutical compositions can be administered orally in forms such as tablets, capsules, pills, powders, sustained release forms, solutions and/or suspensions; by non-intestinal injection in such form as a sterile solution, suspension or emulsion; through a local treatment form such as paste, cream, or ointment; or via a rectal form such as suppositories. The pharmaceutical compositions may be in a unit dosage form that is suitable for precise dosing applications. In addition, the pharmaceutical compositions may include other active ingredients.

Suitable pharmaceutical carriers include water, various organic solvents and various inert diluents or fillers. If necessary, the pharmaceutical compositions may contain various additives, such as spices, adhesives and excipients. For oral administration, tablets can contain various excipients such as citric acid, a variety of disintegrant agents such as starch, alginic acid, and some silicates, and a variety of adhesives such as sucrose, gelatin and Arabic gum. In addition, lubricants including magnesium stearate and talc fillers are commonly used in the production of tablets. The same types of solid components can also be used to formulate soft and hard gelatin capsules. When an aqueous suspension is needed for oral administration, the active compound can be mixed with a variety of sweeteners or flavoring agents, pigments or dye combinations. If necessary, a variety of emulsifiers can be employed or suspensions generated; diluents such as water, ethanol, propylene glycol, glycerin, or their combination can be utilized. The above-described pharmaceutical compositions are preferably administered orally, in the tablet or capsule form.

In another embodiment, the present invention provides use of the compounds of this invention in the manufacturing of medicaments that are useful for the treatment or prevention of non-malignant over-hyperplasia diseases in mammals. The non-malignant over-hyperplasia diseases can be a benign skin hyperplasia or a benign pro static hyperplasia.

In another embodiment, the present invention provides use of the compounds of this invention in the manufacturing of medicaments that are useful for the treatment or prevention of mammalian pancreatitis, kidney disease, cancer, angiogenesis or angiogenesis-related diseases. Compounds of this invention can be used to treat or prevent diseases selected from, but not limited to, tumor angiogenesis, chronic inflammatory diseases such as rheumatoid arthritis, atherosclerosis, skin diseases such as psoriasis and scleroderma, diabetes-induced skin diseases, diabetic retinopathy, premature retinopathy, age-related degeneration stains, hemangioma, glioma, Kaposi internal tumor, ovarian cancer, breast cancer, lung cancer, pancreatic cancer, lymphoma, prostate, colon and skin tumors and their complications.

Among the mammals mentioned herein, human beings are preferred.

Another purpose of this invention is to provide a method for treating malignant tissue hyperplasia in mammals. This treatment method includes application of an effective amount of compounds and/or the pharmaceutical compositions described above to mammalian patients with hyperplasia disease. In some embodiments, the treatment method also includes use of MMP (matrix metalloproteinase) inhibitor, VEGFR (vascular endothelial growth factor receptor) kinase inhibitors, HER2 inhibitor, VEGFR antibody drugs, and/or endostatin drugs. In some other embodiments, the treatment method also includes using one or more anti-tumor agents such as mitotic inhibitors, alkylating agents, anti-metabolites, tumor antibi-otics, growth factor inhibitors, cell cycle inhibitors, enzymes, enzyme inhibitors, biological response modifiers, anti-hormone drugs and so on. The anti-tumor agents can be selected from carboplatin, paclitaxel, gemcitabine, methotrexate, 5-FU, camptothecin, cyclophosphamide, BCNU and other medications.

In another embodiment of this invention is to provide a method for the treatment of diseases caused by tyrosine kinase dysfunction. This treatment method includes administering to an patient with the disease caused by tyrosine kinase dysfunction an effective amount of the compounds pharmaceutical compositions of this invention. The tyrosine kinase dysfunction-related diseases include, but are not limited to disease of brain, lung, liver, bladder, breast, head and neck, esophagus, gastrointestinal tract, breast, ovary, cervix or thyroid tumors and their complications.

Target diseases for the just described treatment method are preferably selected from brain cancer, lung cancer (such as non-small cell lung cancer (NSCLC)), kidney cancer, bone cancer, liver cancer, bladder cancer, chest cancer, neck cancer, esophageal cancer, gastric cancer, colon cancer, rectal cancer, breast cancer, ovarian cancer, melanoma, skin cancer, adrenal cancer, cervical cancer, lymphoma, or thyroid tumors and their complications.

The above-described methods can be applied in combination with any chemical therapy, biological therapy, or radiation therapy.

In another embodiment, the present invention provides a combined preparation of a compound of the present invention and additional therapeutic agent(s) for simultaneous, separate or sequential use in therapy.

The above-described treatment method can further include application of anti-EGFR antibodies, anti-EGF anti-bodies, or both, in the same treatment.

The dosage of the active ingredient or compound when administered will be determined by the individual needs of the patient to be treated, administration route, severity of disease or illness, dosing schedule, as well as evaluation and judgment of the designated doctor. However, based on the active compound, the preferred range of the effective dosage can be approximately 0.01-100 mg daily per kilogram of body weight; or more preferably 0.1-30 mg per day per kilogram of body weight in single or separate doses. In some cases, it is more suitable to apply the lower end of the above-described dosage range, while in other cases the higher dosages may be used without causing harmful side effects.

The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from one to four times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims. All literature publications cited herein are incorporated by reference in their entirety.

What is claimed is:

1. A compound of formula I

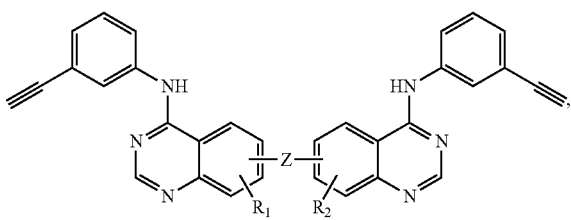

(I)

or a pharmaceutically acceptable salt thereof, wherein:
$R_1$ and $R_2$ are each independently —O-alkylene-$OCH_3$;
Z is a linker selected from the group consisting of: —O-(alkylene-$X_1$)$_m$-alkylene-($X_2$-alkylene)$_n$-O—, —O-(alkylene-$X_1$)$_m$-cycloalkylene-($X_2$-alkylene)$_n$-O—, and —O-(alkylene-$X_1$)$_m$-heterocyclylene-($X_2$-alkylene)$_n$-O—;
$X_1$ and $X_2$, at each occurrence, are independently —O—, —$NR_3$—, —S—, —SO—, or —$SO_2$—;
m and n, at each occurrence, are independently selected from integers from 1 to 10;
$R_3$ is H, —$COR_4$, or —$SO_2R_4$; and
$R_4$ is alkyl or cycloalkyl.

2. The compound of claim 1, or a pharmaceutically acceptable salt thereof, wherein $X_1$ and $X_2$ are each oxygen (—O—).

3. The compound of claim 1, or a pharmaceutically acceptable salt thereof, wherein:
$R_1$ and $R_2$ are each independently —O—($CH_2CH_2$)$_i$—$OCH_3$, where i=1, 2, or 3; and
$X_1$ and $X_2$ are each oxygen (—O—).

4. The compound of claim 1, or a pharmaceutically acceptable salt thereof, wherein:
$R_1$ and $R_2$ are each —O—$CH_2CH_2$—$OCH_3$;
Z is a linker selected from the group consisting of: —O—($CH_2CH_2O$)$_m$—($CH_2$)$_y$—($OCH_2CH_2$)$_n$—O—, —O—($CH_2CH_2O$)$_m$—($C_3$-$C_{10}$)cycloalkylene-($OCH_2CH_2$)$_n$—O—, and —O—($CH_2CH_2O$)$_m$-(3- to 10-membered)heterocyclylene-($OCH_2CH_2$)$_n$—O—;
m and n, at each occurrence, are independently selected from integers from 1 to 10; and
y is an integer from 2 to 10.

5. The compound of claim 1, or a pharmaceutically acceptable salt thereof, wherein:
$R_1$ and $R_2$ are each —O—$CH_2CH_2$—$OCH_3$;
Z is a linker selected from the group consisting of: —O—($CH_2CH_2O$)$_m$—$CH_2CH_2$—($OCH_2CH_2$)$_n$—O—, —O—($CH_2CH_2O$)$_m$—($C_3$-$C_{10}$)cycloalkylene-($OCH_2CH_2$)$_n$—O—, and —O—($CH_2CH_2O$)$_m$-(3- to 10-membered)heterocyclylene-($OCH_2CH_2$)$_n$—O—; and
m and n, at each occurrence, are independently selected from integers from 1 to 10.

6. The compound of claim 1, or a pharmaceutically acceptable salt thereof, wherein:
$R_1$ and $R_2$ are each —O—$CH_2CH_2$—$OCH_3$; and
Z is —O—($CH_2CH_2O$)$_m$—$CH_2CH_2$—($OCH_2CH_2$)$_n$—O—, wherein m and n are independently integers selected from 1 to 10.

7. The compound of claim 1, or a pharmaceutically acceptable salt thereof, wherein:
$R_1$ and $R_2$ are each —O—$CH_2CH_2$—$OCH_3$; and
Z is —O—($CH_2CH_2O$)$_m$—$CH_2CH_2$—($OCH_2CH_2$)$_n$—O—, wherein m and n are each independently 1, 2, or 3.

8. The compound of claim 7, or a pharmaceutically acceptable salt thereof, wherein m and n are each independently 1 or 2.

9. The compound of claim 1, selected from the group consisting of:

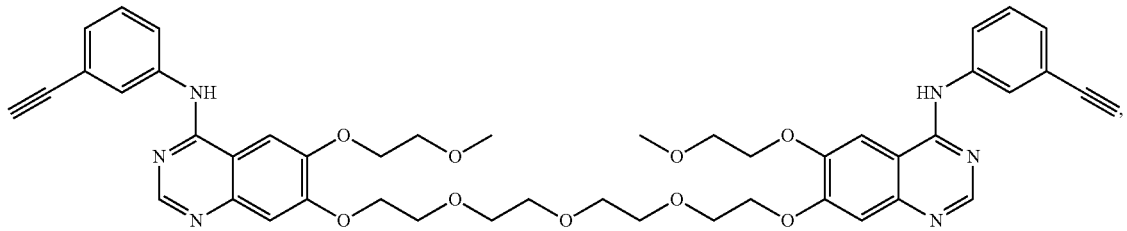

-continued

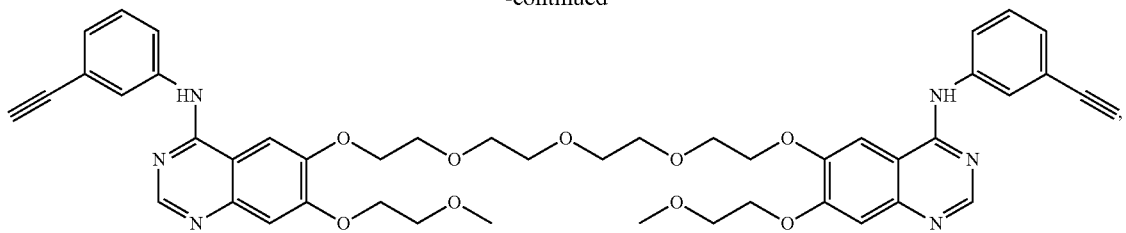

and

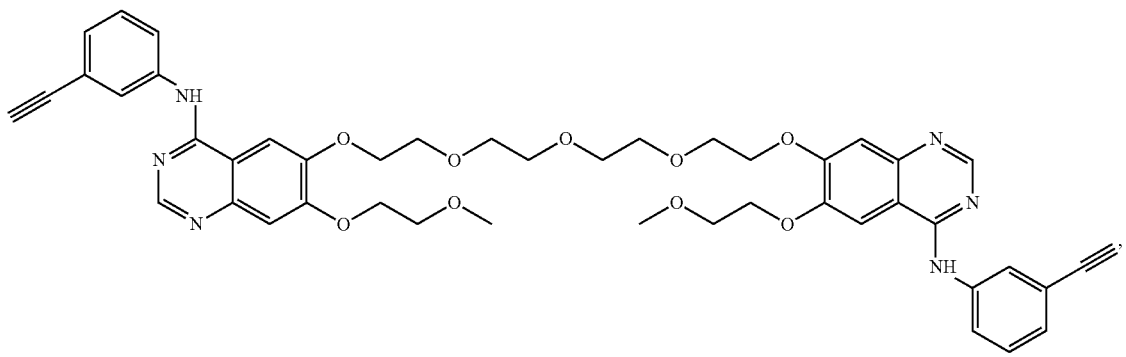 [SMILES: C#Cc1cccc(Nc2ncnc3cc(OCCOCCOCCOCCOc4cc5c(Nc6cccc(C#C)c6)ncnc5cc4OCCOC)c(OCCOC)cc23)c1]

or a pharmaceutically acceptable salt thereof.

10. The compound of claim 1, having the structure of:

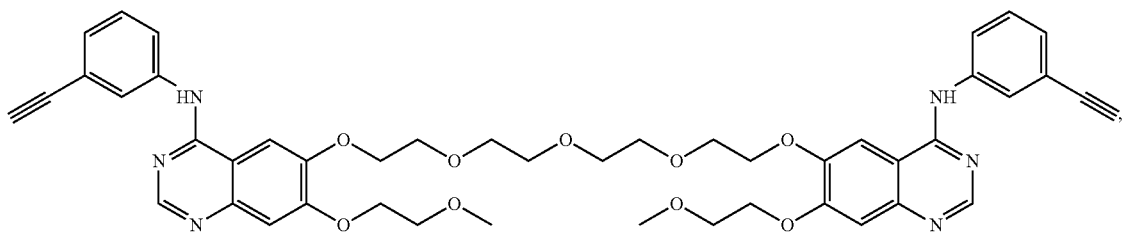

or pharmaceutically acceptable salt thereof.

11. A method for preparing a compound of claim 1, or a pharmaceutically acceptable salt thereof, the method comprising:

1) reacting the compound of formula (6a) with an alkylating agent to get the compound of formula (7):

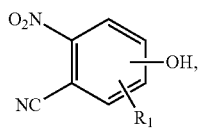
(6a)

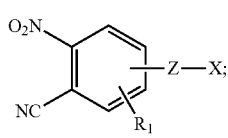
(7)

2) reacting the compound of formula (7) with the compound of formula (6b) to get the compound of formula (8):

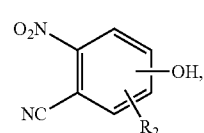
(6b)

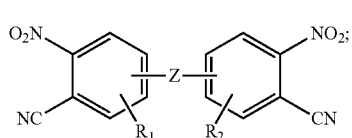
(8)

3) reducing the compound of formula (8) to get the compound of formula (9):

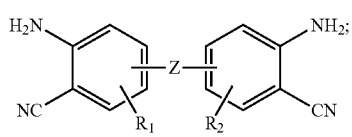
(9)

4) reacting the compound of formula (9) with DMF-DMA to get the compound of formula (10):

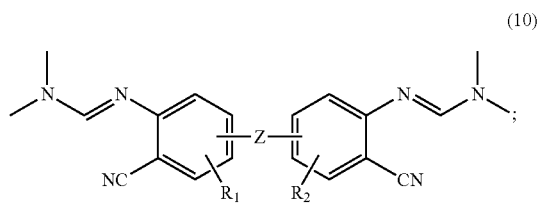
(10)

and 5) reacting the compound of formula (10) with 3-ethynylaniline to get the tethered quinaziline dimer compound of formula (I):

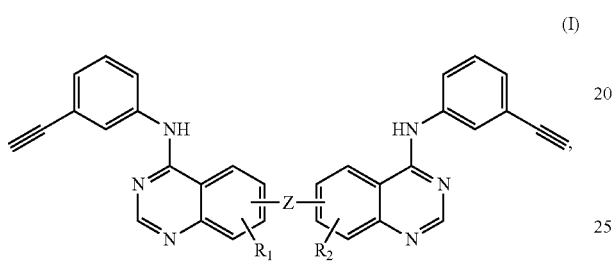
(I)

wherein $R_1$, $R_2$, Z are defined in claim 1, and X is a leaving group selected from halogen and sulfonates.

12. The method of claim 11, wherein the compounds of formula (6a) and (6b) are prepared by a method comprising steps of:

a) reacting the compound of formula (2)

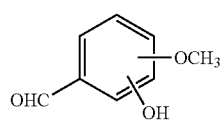
(2)

with an alkylating agent of formula X-alkylene-O—CH$_3$, wherein X is a leaving group, to get a compound of formula (3a) or (3b):

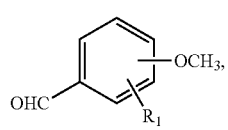
(3a)

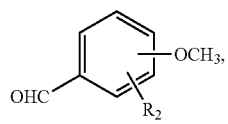
(3b)

wherein $R_1$ and $R_2$ are each independently —O-alkylene-O—CH$_3$;

b) reacting the compound of formulae (3a) or (3b) with NH$_2$OH, or a salt thereof to give corresponding oxime adducts, followed by dehydrating the oxime adducts to get nitrile compounds of formula (4a) or (4b), respectively:

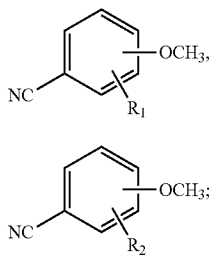
(4a)

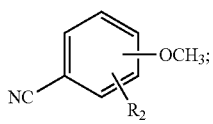
(4b)

c) nitrating the compound of formula (4a) or (4b) using a nitrating agent to get the corresponding nitro-compound of formula (5a) or (5b), respectively:

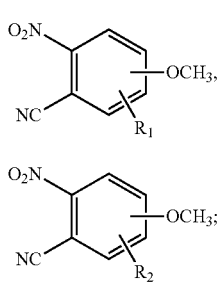
(5a)

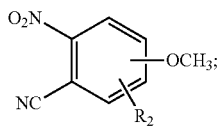
(5b)

d) selectively demethylating the compound of formula (5a) or (5b) to get the compound of formulae (6a) or (6b), respectively:

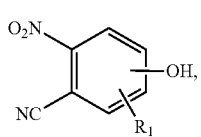
(6a)

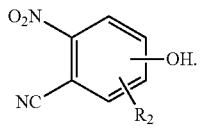
(6b)

13. The method of claim 11, wherein:

$R_1$ and $R_2$ are each independently —O—(CH$_2$CH$_2$)$_i$—OCH$_3$, wherein i=1, 2, or 3; and Z is —O—(CH$_2$CH$_2$O)$_m$—CH$_2$CH$_2$—(OCH$_2$CH$_2$)$_n$—O—, wherein m and n are independently integers selected from 1 to 10.

14. The method of claim 11, wherein:

$R_1$ and $R_2$ are each —O—CH$_2$CH$_2$—OCH$_3$; and

Z is —O—(CH$_2$CH$_2$O)$_m$—CH$_2$CH$_2$—(OCH$_2$CH$_2$)$_n$—O—, wherein m and n are each independently 1, 2, or 3.

15. A pharmaceutical composition comprising a compound of claim 1, or a pharmaceutically acceptable salt thereof, and a pharmaceutically acceptable carrier.

16. A method of treating a patient suffering from lung cancer, comprising administering to said patient a therapeutically effective amount of a compound of claim 1, or a pharmaceutically acceptable salt thereof.

17. The method of claim 16, wherein the compound is administered at a dosage between 1 and 2,000 mg per day, in a single dose or in the form of individual doses for one to four times per day.

18. The method of claim 16, wherein the compound is administered orally in a dosage form selected from tablets, capsules, pills, powders, sustained release forms, solutions, suspensions; by non-intestinal injection in a dosage form selected from sterile solutions, suspensions and emulsions; through local treatment in a dosage form selected from pastes, creams, and ointments; or via a rectal dosage form of suppositories.

* * * * *